United States Patent
Mazzell et al.

(10) Patent No.: US 8,283,500 B2
(45) Date of Patent: Oct. 9, 2012

(54) SEPARATION/PURIFICATION OF DESFLURANE FROM HYDROGEN FLUORIDE

(75) Inventors: Paul Mazzell, Aiken, SC (US); Barry Jones, Martinez, GA (US); Neville Pavri, Evans, GA (US); Joel Swinson, Evans, GA (US)

(73) Assignee: Halocarbon Products Corporation, River Edge, NJ (US)

( * ) Notice: Subject to any disclaimer, the term of this patent is extended or adjusted under 35 U.S.C. 154(b) by 428 days.

(21) Appl. No.: 11/815,673

(22) PCT Filed: Feb. 9, 2006

(86) PCT No.: PCT/US2006/004829
§ 371 (c)(1),
(2), (4) Date: Aug. 7, 2007

(87) PCT Pub. No.: WO2006/121479
PCT Pub. Date: Nov. 16, 2006

(65) Prior Publication Data
US 2008/0306309 A1     Dec. 11, 2008

Related U.S. Application Data

(60) Provisional application No. 60/653,146, filed on Feb. 15, 2005.

(51) Int. Cl.
*C07C 43/00* (2006.01)

(52) U.S. Cl. .......................... 568/683; 568/681; 568/682
(58) Field of Classification Search .................. None
See application file for complete search history.

(56) References Cited

U.S. PATENT DOCUMENTS

| 1,676,735 | A |   | 7/1928  | Keyes         |         |
|-----------|---|---|---------|---------------|---------|
| 3,535,388 | A | * | 10/1970 | Terrell       | 568/684 |
| 5,026,924 | A |   | 6/1991  | Cicco         |         |
| 5,205,914 | A |   | 4/1993  | Rozov et al.  |         |
| 5,230,778 | A |   | 7/1993  | Gavlin et al. |         |
| 6,800,786 | B1| * | 10/2004 | Rozov et al.  | 568/683 |

FOREIGN PATENT DOCUMENTS

KR   10 2002 7012180   10/2009

* cited by examiner

*Primary Examiner* — Johann Richter
*Assistant Examiner* — Clinton Brooks
(74) *Attorney, Agent, or Firm* — Norris McLaughlin & Marcus, PA

(57) ABSTRACT

An azeotrope comprising desflurane ($CF_3CFHOCF_2H$) and hydrogen fluoride (HF). The azeotrope can be prepared by fractionally distilling a crude mixture of desflurane and HF. Purer desflurane can be readily and easily separated from the azeotrope. It is emphasized that this abstract is provided to comply with the rules requiring an abstract which will allow a searcher or other reader quickly to ascertain the subject matter of the technical disclosure. It is submitted with the understanding that it will not be used to interpret or limit the scope or meaning of the appended issued claims.

26 Claims, No Drawings

SEPARATION/PURIFICATION OF DESFLURANE FROM HYDROGEN FLUORIDE

BACKGROUND OF THE INVENTION

1. Field of the Invention

The present invention relates generally to the preparation of desflurane ($CF_3CFHOCF_2H$), which is a well known inhalation anesthetic.

2. Description of Related Art

There are several known processes to manufacture desflurane in which the desired product is obtained mixed with hydrogen fluoride, where the hydrogen fluoride can either be a reagent or can be generated as a byproduct. In all cases the hydrogen fluoride is removed from the desflurane by washing with water. It is known to those skilled in the art that it is very difficult to separate hydrogen fluoride from water, which makes the process both economically and environmentally unfavorable.

One method to prepare desflurane (U.S. Pat. No. 6,054,626) involves the reaction of 2-difluoromethoxy-1,1,1-trifluoroethane ($CF_3CH_2OCF_2H$) with a transition metal fluoride fluorinating agent, where the fluorinating agent is cobalt trifluoride ($CoF_3$). The reaction forms hydrogen fluoride as a by-product. The process according to the examples removes the hydrogen fluoride by-product by washing the crude reaction mixture with water.

Desflurane can also be prepared by the reaction of isoflurane ($CF_3CClHCF_2H$) with excess hydrogen fluoride in the presence of antimony pentachloride, alone or in combination with antimony trichloride (U.S. Pat. Nos. 5,026,924 and 6,800,786). This process removes the highly toxic antimony salts as an aqueous stream along with the hydrogen fluoride by washing the crude reaction mixture with water.

Recently, we have disclosed an invention where we prepared desflurane by reaction of isoflurane and excess hydrogen fluoride over a chromia catalyst (U.S. Provisional Application No. 60/643,301, filed on Jan. 12, 2005, the entire contents of which are hereby incorporated by reference).

There remains a need in the art to discover ways to separate/purify desflurane from crude reaction mixtures comprising hydrogen fluoride, and especially to avoid the need to remove hydrogen fluoride by washing with water.

SUMMARY OF THE INVENTION

These and other objects were met with the present invention. We have discovered that desflurane and hydrogen fluoride, surprisingly, form an azeotrope. We have also discovered that purer desflurane can be separated from this azeotrope in a simple and easy manner, optionally, without washing with water.

Thus, the present invention relates in a first embodiment to the azeotrope itself.

The present invention relates in a second embodiment to a process for producing desflurane ($CF_3CFHOCF_2H$) comprising the following steps:
a) conducting a reaction that produces a crude mixture comprising desflurane and hydrogen fluoride;
b) fractionally distilling from said crude mixture an azeotrope comprising desflurane and hydrogen fluoride; and
c) separating purer desflurane from said azeotrope.

DETAILED DESCRIPTION OF THE INVENTION

In the course of attaining our objective to prepare anesthetic grade desflurane we discovered, unexpectedly, that desflurane forms an azeotrope with hydrogen fluoride. In a preferred embodiment, this azeotrope is substantially free of organic impurities. By "substantially free of organic impurities," we mean that the azeotrope contains less than 1%, preferably less than 0.5%, of organic impurities. In the particularly preferred embodiment described hereinbelow, the azeotrope is lower boiling than HF (boiling point is 19.5° C.) and is enriched in desflurane (boiling point is 23° C.). We also determined that the organic component of this azeotrope, which was distilled from the crude reaction mixture, was greater than 99.7% pure desflurane as determined by GC analysis. This level of purity is well within the specifications for anesthetic grade desflurane and meets our objective except for the HF content in the azeotrope.

Accordingly, another objective of the present invention is to provide a process whereby one can obtain desflurane substantially free of hydrogen fluoride without washing with water. This approach would allow one to recycle hydrogen fluoride and would make the process both more economical and environmentally friendly.

It has been found that fractional distillation of a crude reaction mixture obtained in the manufacture of desflurane, for example, by reacting hydrogen fluoride with isoflurane over a bed of chromia catalyst, results in the removal of desflurane in the form of a desflurane/hydrogen fluoride azeotrope that boils below the boiling point of hydrogen fluoride.

In one particular embodiment, the crude reaction mixture comprises by-product HCl, unreacted isoflurane, unreacted HF and desflurane. The HCl is removed by fractional distillation prior to the removal of desflurane/hydrogen fluoride azeotrope.

The azeotropic composition is enriched in desflurane. The composition of the azeotrope depends on the pressure at which the fractional distillation is carried out. In a preferred embodiment, the fractional distillation is carried out at ambient pressure, at reduced pressure or at elevated pressure. In a particularly preferred embodiment, the fractional distillation is carried out at a pressure of 10 to 220 psig, especially a pressure of 50 to 150 psig. In these preferred embodiments, the fractional distillation can be carried out either as a batch process or a continuous process. In a preferred embodiment, both the reaction and removal of desflurane/hydrogen fluoride azeotropic mixture by distillation at higher pressure would be carried out as a continuous process. Any remaining unreacted hydrogen fluoride and isoflurane may then be recycled to the reaction process.

The collected desflurane/hydrogen fluoride azeotrope can then proceed to a separation method in order to obtain pure desflurane and satisfy our second objective. The recovered hydrogen fluoride can be recycled to the reaction process.

The desflurane/hydrogen fluoride azeotrope can be washed with water to obtain desflurane greater than 99% pure. Since the azeotrope is enriched in desflurane the amount of hydrogen fluoride removed by the water wash is not very high which minimizes HF waste and the environmental problems associated therewith.

However, another approach to more efficiently recover the hydrogen fluoride from desflurane involves cooling the azeotropic mixture to a temperature at which the desflurane and hydrogen fluoride separate into two layers. In a preferred embodiment, the azeotropic mixture is cooled to a temperature ranging from about –20° C. to about –80° C., especially to a temperature ranging from about –35° C. to about –55° C. The desflurane/hydrogen fluoride ratio is different in each layer. The separated layer that is substantially enriched with desflurane can be distilled to obtain the desflurane/hydrogen fluoride azeotrope and excess desflurane as the higher boiling product. Alternatively, the layer that is substantially enriched in desflurane can be washed with water to remove the small amount of hydrogen fluoride left behind. The layer that is enriched in HF can be returned to the reaction/distillation process.

A third method to separate desflurane from hydrogen fluoride involves extracting the desflurane from HF using a suitable organic solvent. The requirements for the solvent are as follows:

a. The solvent should extract desflurane and not extract substantial amounts of HF.
b. The solvent should be easily separable from desflurane, for example by distillation.

| Solvent | % Desflurane extracted |
|---|---|
| HC-0.8 oil* | 84% |
| Isooctane | 15% |
| 1,1,2-Trichloroethane | 58% |

*Mixture of tetrachlorohexafluorobutanes, commercially available as HC-0.8 oil from Halocarbon Products Corporation.

As can be seen from the above table, a variety of solvents are capable of extracting desflurane from HF. CFC and other halogenated solvents appear to be superior for this purpose compared to hydrocarbons. It would appear that chlorofluorocarbons, hydrofluorocarbons, chlorohydrocarbons, perfluoroethers, hydrocarbons and other solvents that satisfy the above mentioned requirements can be used for extraction of desflurane.

The following examples illustrate the present invention and should not be construed in any way as limiting its scope.

EXAMPLES

Example 1

Removal of Desflurane/Hydrogen Fluoride Azeotrope from Crude Reaction Mixture

A 6-ft×2-inch tube was charged with chromia catalyst and isoflurane and 5 mole equivalents of HF were introduced in vapor form at a pressure of 150 psig. The by-product HCl, desflurane, unreacted isoflurane and unreacted HF that exited the tube were collected and distilled at 150 psig to remove HCl. After HCl was removed, the reaction mixture was heated at total reflux. At a pressure of 150 psig, the material collected overhead at 82° C. was the desflurane/hydrogen fluoride azeotrope. The composition of the azeotrope, after analysis was determined to be 85% desflurane and 15% HF, by weight. The table below shows the boiling point and composition of the azeotrope at different pressures.

| Distillation pressure (psig) | Overhead temperature (° C.) | % Desflurane | % HF |
|---|---|---|---|
| 25 | 35 | 82 | 18 |
| 50 | 50 | 85 | 15 |
| 80 | 63 | 85 | 15 |
| 120 | 75 | 85 | 15 |
| 150 | 82 | 85 | 15 |

Example 2

Separation of Desflurane from HF by Cooling to −45° C.

A mixture of desflurane (10.6 grams) and HF (2.7 grams) was cooled in a tube to −45° C. This ratio is the approximate composition of the azeotrope at 25 psig. It was allowed to stay at this temperature for 20 minutes. At this time, the top layer was separated from the bottom layer and weighed (3.1 grams). A portion of the bottom layer (2.4 grams) was removed and analyzed for % HF. Analysis indicated that the lower layer which was substantially enriched in desflurane contained 5% HF by weight.

Example 3

Extraction of Desflurane Using HC 0.8 Oil

A mixture of equal volume of HF and HC-0.8 oil were stirred at 0° C. for 15 minutes and a small amount of desflurane was added to it. The mixture was stirred at 0° C. for 5 minutes and then the layers were allowed to separate. The lower layer was removed. A second extraction with equal volume of HC-0.8 oil was done. Both extracts were analyzed by GC and desflurane was seen in each. The first extraction had twice the amount of desflurane compared to second extraction. The organic extracts were combined and weighed. The amount of desflurane extracted was 84% of theoretical.

It should be understood that the preceding detailed description of the invention is merely a detailed description of one preferred embodiment or of a small number of preferred embodiments of the present invention and that numerous changes to the disclosed embodiment(s) can be made in accordance with the disclosure herein without departing from the spirit or scope of the invention. The preceding detailed description of the invention, therefore, is not meant to limit the scope of the invention in any respect. Rather, the scope of the invention is to be determined only by the appended issued claims and their equivalents.

What is claimed is:
1. An isolated and purified azeotrope comprising desflurane ($CF_3CFHOCF_2H$) and hydrogen fluoride.
2. The azeotrope according to claim 1, which is substantially free of organic impurities.
3. The azeotrope according to claim 1, which boils at a lower temperature than hydrogen fluoride.
4. A process for producing desflurane ($CF_3CFHOCF_2H$), said process comprising the following steps:
   a) conducting a reaction that produces a crude mixture comprising desflurane, unreacted isoflurane, HCl and hydrogen fluoride;
   b) fractionally distilling from said crude mixture HCl and, thereafter, an azeotrope comprising desflurane and hydrogen fluoride; and
   c) separating purer desflurane from said azeotrope.
5. The process according to claim 4, wherein said azeotrope is substantially free of organic impurities.
6. The process according to claim 4, wherein said azeotrope boils at a lower temperature than hydrogen fluoride.
7. The process according to claim 4, where the fractional distillation is carried out at ambient pressure.
8. The process according to claim 7, where the fractional distillation is carried out in a batchwise manner.
9. The process according to claim 7, where the fractional distillation is carried out in a continuous manner.

10. The process according to claim 4, where the fractional distillation is carried out at reduced pressure.

11. The process according to claim 10, where the fractional distillation is carried out in a batchwise manner.

12. The process according to claim 10, where the fractional distillation is carried out in a continuous manner.

13. The process according to claim 4, where the fractional distillation is carried out at elevated pressure.

14. The process according to claim 13, where the fractional distillation is carried out in a batchwise manner.

15. The process according to claim 13, where the fractional distillation is carried out in a continuous manner.

16. The process according to claim 15, where the fractional distillation is carried out at a pressure of 10 to 220 psig.

17. The process according to claim 16, where the fractional distillation is carried out at a pressure of 50 to 150 psig.

18. The process according to claim 4, wherein purer desflurane is separated from the azeotrope by washing with water.

19. The process according to claim 4, wherein purer desflurane is separated from the azeotrope by cooling the azeotrope to a temperature below which a plurality of layers are formed, and then separating a layer that is enriched in desflurane compared to the azeotrope.

20. The process according to claim 19, wherein the temperature ranges from −20° C. to −80° C.

21. The process according to claim 20, wherein the temperature ranges from −35° C. to −55° C.

22. The process according to claim 21, wherein the layer that is enriched in desflurane is washed with water.

23. The process according to claim 21, where the layer that is enriched in desflurane is fractionally distilled.

24. The process according to claim 4, wherein purer desflurane is separated from the azeotrope by solvent extraction using a solvent that can be easily separated from desflurane.

25. The process according to claim 24, wherein the solvent is selected from the group consisting of chlorofluorocarbons, chlorohydrocarbons, fluorinated ethers, hydrofluorocarbons and hydrocarbons.

26. The process according to claim 25, wherein the solvent is HC-0.8 oil.

\* \* \* \* \*